United States Patent
Alexopoulos et al.

(10) Patent No.: US 12,068,076 B1
(45) Date of Patent: Aug. 20, 2024

(54) SYSTEM AND METHOD FOR ASTHMA MONITORING AND PROGNOSIS

(71) Applicants: Aleck Alexopoulos, Salonika (GR); Christodoulos Spagkakas, Salonika (GR)

(72) Inventors: Aleck Alexopoulos, Salonika (GR); Christodoulos Spagkakas, Salonika (GR)

( * ) Notice: Subject to any disclaimer, the term of this patent is extended or adjusted under 35 U.S.C. 154(b) by 371 days.

(21) Appl. No.: 17/315,413

(22) Filed: May 10, 2021

Related U.S. Application Data (60) Provisional application No. 63/022,566, filed on May 10, 2020.

(51) Int. Cl.
| | | |
|---|---|---|
| *G16H 40/67* | (2018.01) | |
| *G01N 1/24* | (2006.01) | |
| *G01N 15/0205* | (2024.01) | |
| *G06F 16/23* | (2019.01) | |
| *G16H 10/20* | (2018.01) | |

(Continued)

(52) U.S. Cl.
CPC ............ *G16H 40/67* (2018.01); *G01N 1/24* (2013.01); *G01N 15/0205* (2013.01); *G06F 16/2365* (2019.01); *G16H 10/20* (2018.01); *G16H 10/60* (2018.01); *G16H 15/00* (2018.01); *G16H 40/20* (2018.01); *G16H 50/20* (2018.01); *G16H 50/30* (2018.01); *G16H 50/70* (2018.01); *G01N 2001/245* (2013.01); *G06N 20/00* (2019.01)

(58) Field of Classification Search
CPC ........ G16H 40/67; G16H 40/20; G16H 10/60; G16H 15/00; G16H 50/30; G16H 50/70; G16H 50/20; G16H 10/20; G06F 16/2365; G01N 1/24; G01N 15/0205; G01N 2001/245; G06N 20/00
See application file for complete search history.

(56) References Cited

U.S. PATENT DOCUMENTS

| | | | |
|---|---|---|---|
| 9,995,667 B2 * | 6/2018 | Hart | ................... G01N 15/0205 |
| 10,820,852 B2 * | 11/2020 | Przybylski | ........... A61B 5/6898 |

(Continued)

FOREIGN PATENT DOCUMENTS

| | | | |
|---|---|---|---|
| EP | 0083162 B1 * | 7/1988 | |
| WO | WO-2012158954 A1 * | 11/2012 | |

(Continued)

OTHER PUBLICATIONS

Lehrer, P. Anger, stress, dysregulation produces wear and tear on the lung. Thorax: 2006; 61: 833-834. (Year: 2006).*

(Continued)

*Primary Examiner* — Jason S Tiedeman
*Assistant Examiner* — Tristan Isaac Evans (57) ABSTRACT

A system and a method for management, prediction, and warning of an asthma condition of an asthma patient is provided which employ a wearable, air-quality device for collecting environmental air quality data relating to the asthma condition in the patient's ambient air, an asthma management application installed on a mobile device of the asthma patient or of a care provider of the asthma patient for collecting daily asthma symptom data for the asthma patient, and a cloud processing platform for analyzing the environmental and symptom data and preparing a next day risk report accessible via the asthma management application.

12 Claims, 8 Drawing Sheets

(51) Int. Cl.
   *G16H 10/60*  (2018.01)
   *G16H 15/00*  (2018.01)
   *G16H 40/20*  (2018.01)
   *G16H 50/20*  (2018.01)
   *G16H 50/30*  (2018.01)
   *G16H 50/70*  (2018.01)
   *G06N 20/00*  (2019.01)

(56) References Cited

U.S. PATENT DOCUMENTS

| | | | | |
|---|---|---|---|---|
| 2012/0203126 | A1* | 8/2012 | Kahlman | A61B 5/412 600/532 |
| 2015/0212057 | A1* | 7/2015 | Darveau | G01N 33/004 73/31.03 |
| 2016/0318368 | A1* | 11/2016 | Alger | G08G 1/096791 |
| 2019/0234921 | A1* | 8/2019 | Ahn | G01N 21/85 |
| 2020/0390400 | A1* | 12/2020 | Ssenyange | G16H 20/10 |
| 2021/0045657 | A1* | 2/2021 | Thomas | A61B 5/0022 |
| 2021/0098085 | A1* | 4/2021 | Bastide | G16H 10/60 |
| 2022/0003894 | A1* | 1/2022 | Shapiro | G01W 1/10 |
| 2022/0175288 | A1* | 6/2022 | Uehara | A61B 5/222 |

FOREIGN PATENT DOCUMENTS

| | | | |
|---|---|---|---|
| WO | WO-2018122227 | A1 * | 7/2018 |
| WO | WO-2018202891 | A1 * | 11/2018 |
| WO | WO-2021081104 | A1 * | 4/2021 |

OTHER PUBLICATIONS

Choudhary, Sanjiw. Sleep effects on breathing and respiratory diseases. Lung India. Vol. 26, Issue 4, Oct-Dec. 2009. (Year: 2009).*

Alsharairi, Naser A. The Effects of Dietary Supplements on Asthma and Lung Cancer Risk in Smokers and Non-Smokers: A Review of the Literature. Nutrients 2019, 11, 725; doi: 10.3390/nu11040725. (Year: 2019).*

Hojaiji, Hannaneh. Temperature and Humidity Calibration of a Low Cost Wireless Dust Sensor for Real Time Monitoring. 2017 IEE Sens Appl Symp (SAS)(2017). Mar. 2017. (Year: 2017).*

A mechanistic modeling system for estimating large-scale emissions and transport of pollen and co-allergens. Efstathiou. Atmospheric Environment 45 (2011) 2260-2276. (Year: 2011).*

Thamrin. Predicting future risk of asthma exacerbations using individual conditional probabilities. J Allergy Clin Immunol 2011; 127: 1494-502. (Year: 2011).*

* cited by examiner

SYSTEM AND METHOD FOR ASTHMA MONITORING AND PROGNOSIS

REFERENCE TO RELATED APPLICATION

The present application claims priority from U.S. provisional 63/022,566 filed on May 10, 2020 with the United States Patent and Trademark Office and which is incorporated herein for all purposes.

FIELD OF THE INVENTION

The present invention relates generally to the field of digital and personalized health. More specifically, the present invention relates to a deep monitoring, prediction, and warning system and method for people with asthma. The system comprises a wearable air quality device, a mobile device, and a cloud processing platform. The system and method provide personalized solutions for intelligent monitoring and management of asthma that enables healthier living with asthma, improved respiratory health, as well as prediction and minimization of asthma attacks.

BACKGROUND

Asthma is a serious chronic respiratory disease affecting all ages with major socio-economic consequences. Asthma causes 250 k deaths per year worldwide and it is the leading cause of hospitalization for children under the age of 18, e.g., 300,000/yr in the US. Indeed, nearly half (44%) of all of all asthma hospitalizations are for children. From an economics perspective, the annual cost of hospitalizations due to asthma in the US and Europe is about $120b and the total cost worldwide is about $300b. The average direct and indirect costs for people with severe asthma are estimated to add up to about $6,000/yr per individual.

Despite the huge economic burden and increased susceptibility of children, asthma management is currently insufficient and needs to be improved. To a large extent many of the hospitalizations due to asthma and even deaths could be avoided with better management. Parents of children with asthma, especially of the severe type, are urgently seeking improved and effective solutions which currently do not exist. Therefore, improved asthma management and new predictive tools are needed in order to achieve healthy living with asthma and minimization of asthma attacks.

A technical difficulty of asthma management stems from the wide range of environmental triggers, e.g., pollen, pollutants, and particulates, etc., together with the differences in the state of inflammation and sensitivities to these triggers between individuals. The exposure histories, sensitivities, and inflammation vary from day to day and between individuals. Although these difficulties and issues are currently well acknowledged in the medical literature, they have not been studied in depth with populations due to the lack of appropriate devices, data, and computational tools. It is not surprising that there are no commercial products or even proposed solutions taking under consideration the aforementioned aspects of asthma management.

Proposed solutions do not offer predictive capabilities for asthma patients or substantial improvements in respiratory health or effective management of asthma. Also, existing solutions do not focus on the patient instead they are physician or device centric.

Therefore, there exists a need for personalized point-of-care solutions that consider the exposure and symptom histories of the asthma patient, and take into account direct triggers, e.g., pollen.

SUMMARY OF THE INVENTION

These and other problems of the prior art are solved by the present invention of a system and method for monitoring, predicting and warning people with asthma. The present invention provides a personalized point-of-care solution that considers the exposure and symptom histories of the asthma patient, and takes into account direct triggers including pollen.

The present invention method and system provide personalized feedback to the user, taking into account the user's daily symptoms and air exposure, which includes a detailed risk analysis of the possibility of a next day asthma attack.

An embodiment of the invention is directed to a system for the intelligent monitoring and management of asthma of a user of the system. The system comprises:
  an air-quality wearable air-quality device including at least one sensor for measuring at least one of an environmental pollutant, particulates, and pollen in the ambient air of the user;
  an asthma management application installed on a mobile device of the user;
  at least one cloud database; and
  at least one cloud software,
  wherein the asthma management application is configured for reading and processing data received from the wearable air-quality device, enabling symptom data entry by the user, sending data to the at least one cloud database for processing by the at least one cloud software, accepting data from the cloud database, and presenting an asthma risk report to the user, and
  wherein the at least one cloud database and the at least one cloud software are configured for storing and processing user exposure and symptom data.

The air quality wearable air-quality device may further include at least one sensor for measuring pollen,
  means for sampling the ambient air including a fan for providing a controlled flow rate to the sensor for pollen particulates;
  a communication device for communicating with the user mobile device;
  a processor operably coupled with the sensors and the communication device for receiving the data collected from the sensors and transferring the collected data to the asthma management application of the mobile device, and
  a rechargeable battery operably coupled with the sensors, processor, and communication device for providing power.

These and other advantages of the present invention system will become better understood by those skilled in the art of the present invention from the following detailed description in conjunction with the accompanying drawings.

BRIEF DESCRIPTION OF THE DRAWINGS

By reference to the appended drawings, which illustrate exemplary embodiments of this invention, the detailed description provided below explains in detail various features, advantages and aspects of this invention. As such, features of this invention may be more clearly understood from the following detailed description considered in conjunction with the following drawings. The exemplary embodiments illustrated in the drawings are not intended to be considered limiting of the scope of the invention for the invention may be implemented with other equally effective embodiments.

DETAILED DESCRIPTION

According to an embodiment of the present invention, the system comprises a wearable air-quality device, a smart mobile phone device and cloud databases and software. (see FIG. 1). The wearable air-quality device monitors parameters (which are known to detrimentally affect the asthma condition, e.g., airborne particulates) indicative of the quality of air that the user is exposed to. The wearable air-quality device sends the exposure data (also referred to herein as Exposure Information or EI) to an application installed on the smart mobile phone device (also referred to herein as Asthma Management Application or AMA) where the data is processed (e.g., labelling, smoothing, completion, reduction, compression) and then directed to the cloud databases and software. The AMA can access the cloud processing platform and prompt the user to enter their daily symptoms relating to their asthma condition (also referred to herein as Symptom Information or SI) which are then directed to the cloud software. The cloud software analyzes the exposure and symptom information of the user and provides key information concerning the asthma condition of the user as well as the risk (possibility) of a next day asthma attack (also referred to herein as risk information or RI) to the user via the AMA. All relevant information (e.g., exposure, symptom, and risk information, cloud software data) is distributed to a cloud processing platform which includes databases, software and a microprocessor for storing and processing the received data, creating the individualized risk report and sending back to the AMA on the user mobile device. The cloud databases together with the cloud software and microprocessor are referred to herein as the cloud processing platform or CPP.

Figure 2A:
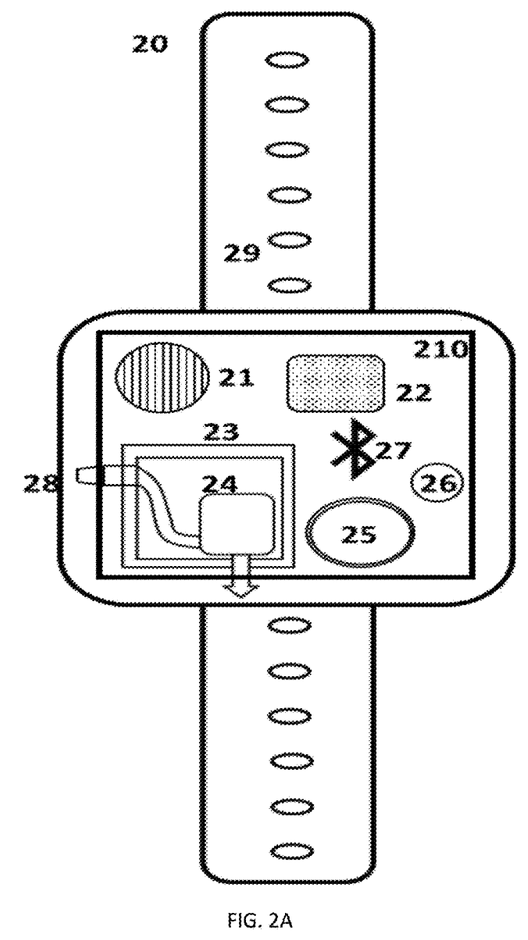
FIG. 2A is a simplified schematic of a wearable air-quality device according to an embodiment of the application including a microprocessor 210, a first sensor 21 for at least one gas pollutant, a second sensor 22 for environmental data, and a third sensor for particulates including pollen 23, the sensor 23 including an air inlet 28, and a fan 24, battery 25, LED 26, and band 29.

The wearable air-quality device may include at least one of different sensors for measuring environmental pollen, particulates, and one or more pollutant, (also referred to herein as the 3Ps), that can trigger or influence an asthma attack (see FIG. 2A). The wearable air-quality device may include at least one sensor for monitoring one or more environmental conditions such ambient temperature, ambient humidity (e.g., temperature sensor, humidity sensor). The at least one sensor may be a multi-sensor. The at least one sensor may be a digital sensor meaning that the measured exposure info is provided by the sensor in digital form. A pollutant sensor may measure one of ozone $O_3$, sulfur dioxide $SO_2$, nitrogen oxides $NO_x$, volatile organic compounds VOCs, ammonia $NH_4$, carbon dioxide $CO_2$, and carbon monoxide CO. Various sensors may be used provided that they are compact and can be readily mounted on the wearable air-quality device. For example, the at least one sensor may be a solid-state, physicochemical, and/or optical sensor. The wearable air-quality device includes a communication device such as a data transmitter for providing to the AMA in the user mobile device and the CPP the user's personalized daily EI received from the at least one sensor. The exposure information together with the user's daily SI are analyzed by the system to provide personalized, predictive, and protective metrics and RI to the user. The communication device of the wearable air-quality device also communicates with the at least one sensor for receiving the EI from the at least one sensor.

The wearable air-quality device further includes an energy management system for intermittent operation of an airflow fan to minimize energy consumption. The device also includes an intermittent switch that alters the airflow pathway in a way that changes the scattering pathlength of the optical sensor's laser. (FIG. 2B) This component of the invention enables measurement of particles in the size range of 10-100 μm which includes environmental pollen.

Figure 2B:
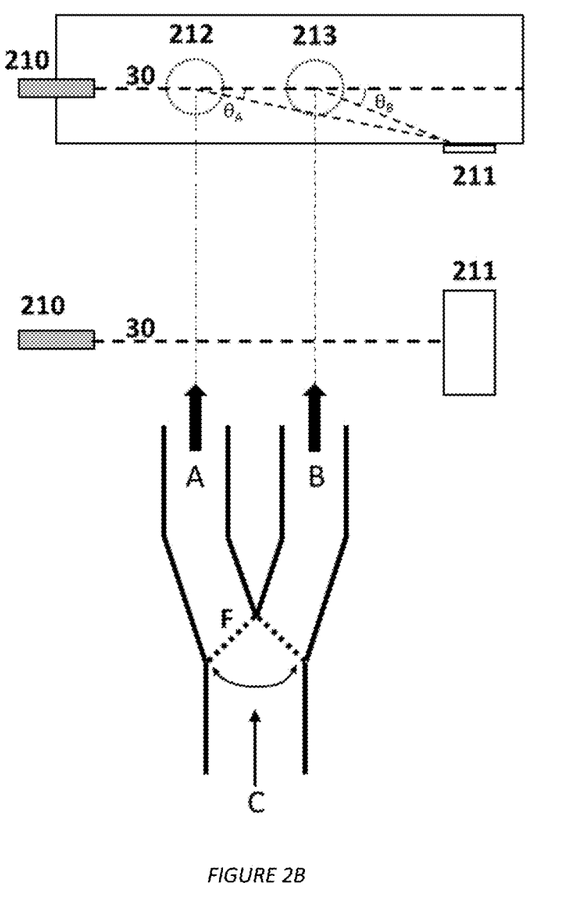
FIG. 2B is a simplified schematic of an optical module of the wearable air-quality device (see FIG. 2A), according to an embodiment of the application including a bifurcated airflow pathway dividing into two paths with pathway flap F for selecting one path, laser pathway 29, laser emitter 210, laser sensor 211 indicating the airflow pathway cross-sections 212 and 213.

The optical sensor module is modified in terms of the location of the airflow intersection with the laser pathway in a manner that alters the scattering angle and leads to the detection of larger dispersed entities, e.g., pollen.

The output from the optical sensor module is post-processed to account for the different scattering angles to determine the actual particle sizes of the particulates.

The wearable air-quality device includes a microprocessor for controlling the operations of the at least one sensor, the communication device, the airflow fan, and the energy management system.

Figure 5:
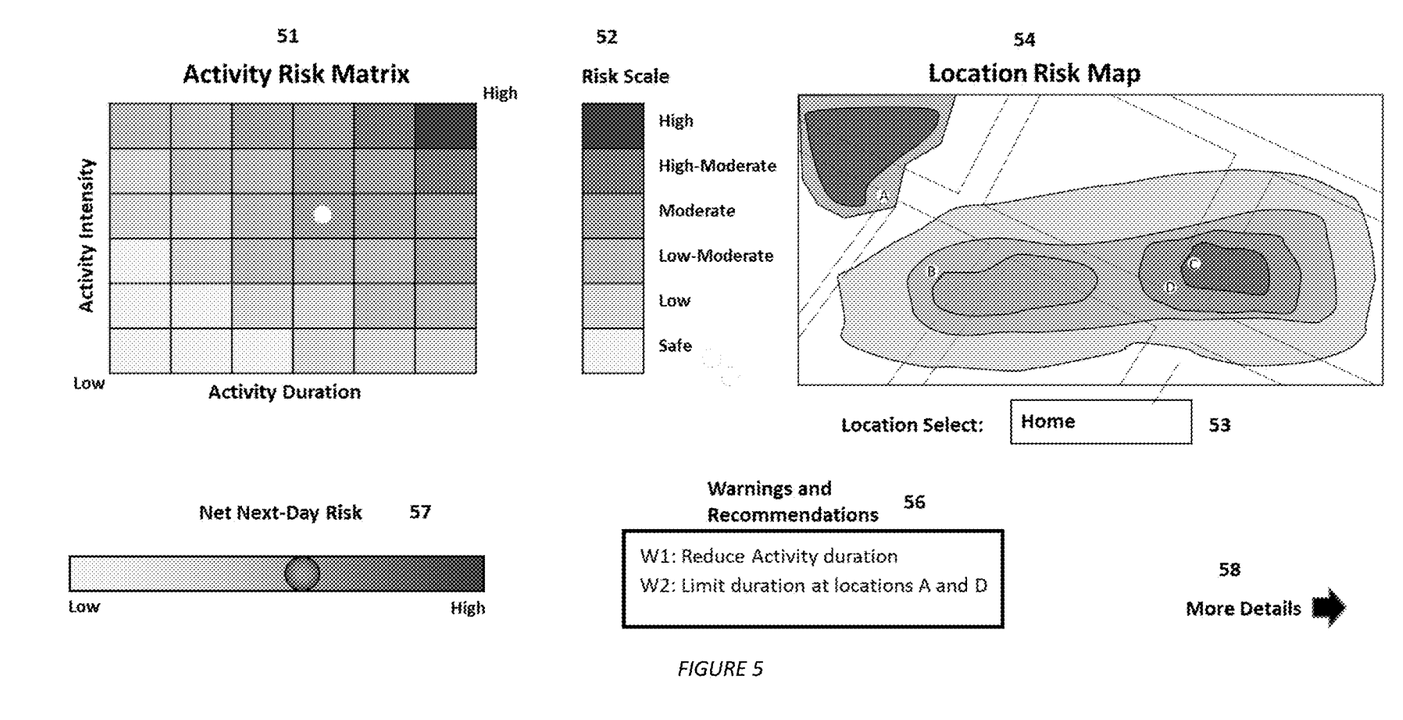
FIG. 5 is a schematic of the application interface related to risk information provided to the user through the AMA.

The AMA may perform the following tasks see (FIG. 3):
processing, compressing, and labeling exposure information received from the wearable air-quality device before sending it to the cloud processing platform,
collecting and processing symptom information of an individual via an asthma symptom questionnaire (e.g., related to shortness of breath, quality of sleep, use of inhaler), before sending it to the CPP, receiving from the CPP and providing RI to the user (generated from the cloud processing system) as well as their exposure history, their symptom history, status of asthma and individual sensitivity, and recommendations by the system in terms regions to avoid, user activity, and possibility of an asthma attack (see FIG. 5).

In an embodiment, the AMA may also include an additional user input interface to allow the user to record various aspects of the user's life and wellness including, for example, dietary data, subjective stress reports, quality of sleep, and the like.

The invention system may be implemented as a single-user version or a multi-user version. The single-user version is suitable for first users and users in isolated areas. The multi-user version is ideal for multiple users residing in the same area, e.g., an urban region. In an embodiment of the invention the single- and multi-user versions employ the same device, the same AMA, but different cloud processing platforms. Specifically, the multi-user cloud databases consist of several volumes corresponding to different urban regions, each volume including the relevant databases from all the users of that region. The multi-user cloud software is an extended version of the single-user cloud software.

According to a single-user embodiment, the cloud software includes the following key elements (see FIG. 5):
- a software for establishing pollen type, concentration levels (using historical pollen, e.g., daily or weekly averaged pollen type and concentration), and weather conditions, i.e., temperature and humidity data in the user vicinity, by employing Machine Learning approaches. This software operates alternatively, or complementarily, to the modified optical system of the wearable air-quality device (see FIG. 2B),
- a user sensitivity matrix analysis via Machine Learning classification techniques or other
- a dynamic correlation between symptom and exposure information, (e.g., via recursive neural net, RNN, or nonlinear autoregressive exogenous model, NARX, techniques with increments of one day)
- a risk analysis based on a hazard matrix approach, user activity (duration and intensity) as well as expected location-dependent next day exposure (based on stationary air-quality stations and the user's exposure history).

The cloud software delivers a detailed status report to the user (e.g., sensitivity profile, exposure history, cumulative exposure, symptom history, correlation metrics) as well as next-day risk information and warnings.

The multi-user version of the cloud software will perform—in addition to the single-user version—the following:
- analysis of dynamic exposure trajectories from multiple users to generate, integrating other data from air-quality analysis stations, Environmental Exposure Maps (herein referred to as EEMs)
- extrapolation from a sequence of exposure maps over several days to predict the EEMs of the 3Ps for the following day taking into account meteorological information and data from air-quality analysis stations
- multivariate and multilevel correlations between exposure and symptom histories and between individuals (e.g., via Machine Learning classification methods) based on data obtained from multiple users
- multi-user risk analysis, extending the single-user approach with cross-user correlations.

Altogether the system integrates collected data, monitors exposure, performs multivariate correlations, identifies individual's sensitivities, and provides current status and probabilities of next day asthma attacks.

Figure 6:
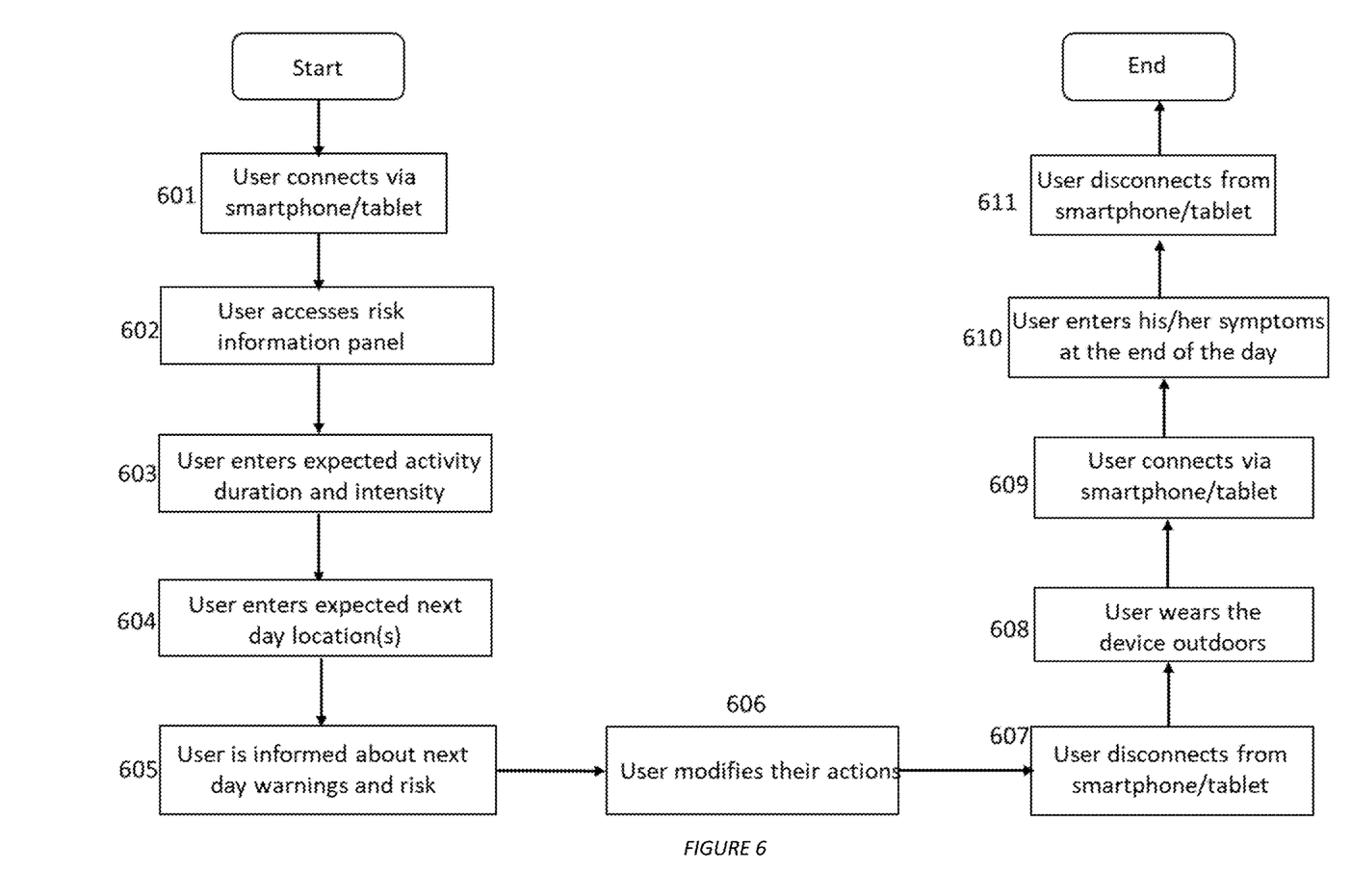
FIG. 6 is a simplified flowchart of asthma monitoring according to an embodiment of the present invention indicating a daily use of the AMA by a user.

According to an embodiment of the invention the user may access the AMA on a daily basis to establish their risk based on their expected activity (i.e., duration and intensity) and their exposure (i.e., locations) during the day (see FIG. 6). The user then adjusts and modifies their actions for the day according to the provided risk information and warnings. At the end of the day the user accesses the AMA to enter their symptom information by answering a questionnaire consisting of multichoice questions and/or graphical rankings of their symptom severity over a given range.

The present invention system and method can significantly reduce the asthma attack hospitalization because the user may interact real time with the AMA, and receive predictions and warnings according to their exposure and sensitivity profile. Therefore, the present invention prediction and warning method and system provides an elegant and simple solution that provides value:
- to the users: by allowing them to save time and money avoiding asthma attacks.
- to the doctors and hospitals: by improving the quality of their service and efficiency of operations
- to the Health Insurance Agencies: by improving effectiveness and efficiency and decreasing annual costs per patient.

The present invention is positioned well beyond the prior art and constitutes a completely original approach to monitor and manage the condition of asthma patients. The invention employs the wearable air-quality device, the AMA and the cloud processing platform. In a preferred embodiment, it allows the monitoring of exposure of all 3Ps (pollutants, particulates, pollen) and with the use of cloud software can determine asthma trigger sensitivity and exposure/symptom correlations and provide predictive next-day risk analysis for the user.

In an embodiment, the present invention delivers to the user: a comprehensive exposure history in terms of the 3Ps, an asthma status and sensitivity profile, and exposure warnings based on long-term exposure to specific irritants (e.g., particulates) and short-term exposure to specific triggers (e.g., pollen). These constitute a significant advantage compared to the state of art. The present invention system and method predicts 60%, or more, of severe asthma attacks.

Another advantage is that a user can purchase their subscription according to asthma severity selecting basic, premium or platinum subscription. Basic subscription provides exposure/symptom summary and status report, premium subscription provides basic plus single warning metrics and simple sensitivity and correlation info, and platinum subscription provides premium plus multi warnings and detailed sensitivity and correlation info.

The mobile App prompts the user to enter asthma symptom related information by answering an asthma specific questionnaire.

The system may further provide feedback to the user via the mobile App which provides next-day warnings with additional risk analysis metrics related to outdoor or indoor living as well as duration and intensity of physical activity.

In an embodiment, the user may enter in the asthma management application life-style information relevant to or influencing the respiratory disease, e.g., dietary, sleep, and stress. Medical data including examination results, spirometry test including FEV1 are used for improved monitoring of the condition of the user may be entered in the asthma management application. Allergy scans may be employed to assist in estimating the initial sensitivity profile of the user.

The cloud software may further include, a sensitivity matrix representing the varying sensitivity of the user to triggers based on the user's recent (up to 5 days or more) exposure and symptom data, exposure/symptom correlation providing means for predicting next day risk of an asthma attack for the user including conditional risk analysis metrics related to outdoor or indoor living as well as duration and intensity of physical activity.

Figure 1:
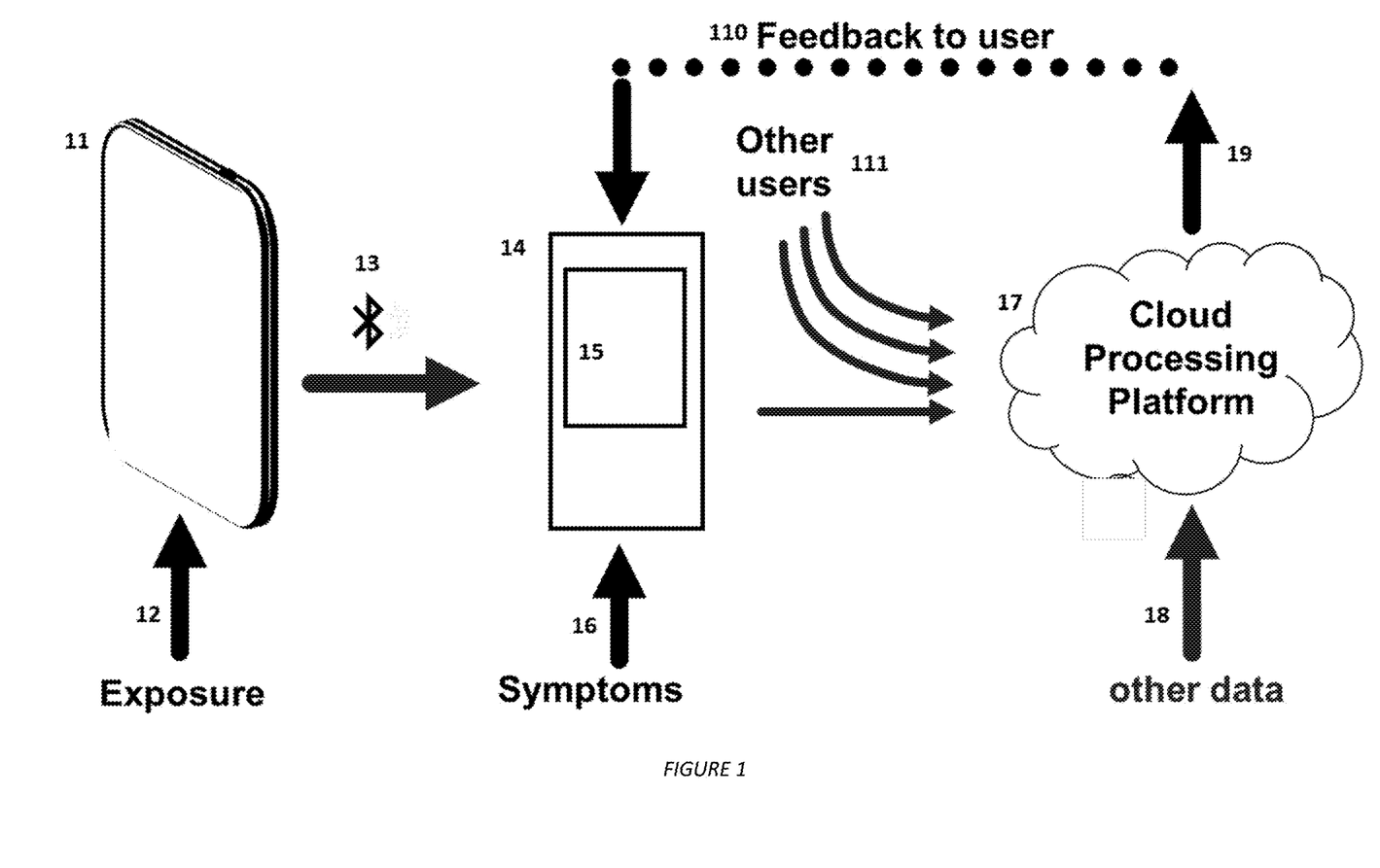
FIG. 1 is a schematic of a system for asthma management according to an embodiment of the present invention, including a wearable air-quality device 11, a smart phone 14 with an asthma management application 15, and a cloud processing platform 17 including at least one database and software for management of symptom and exposure information from one or more users as well as software to process the symptom and exposure information into risk information.

Referring now to FIG. 1, there is provided an asthma management system comprising a wearable air-quality device 11, an AMA 15, in a mobile device 14 such as, for example, a smart phone, a tablet, lap top, desk top and a cloud processing platform 17 including at least one database and software.

Figure 3:
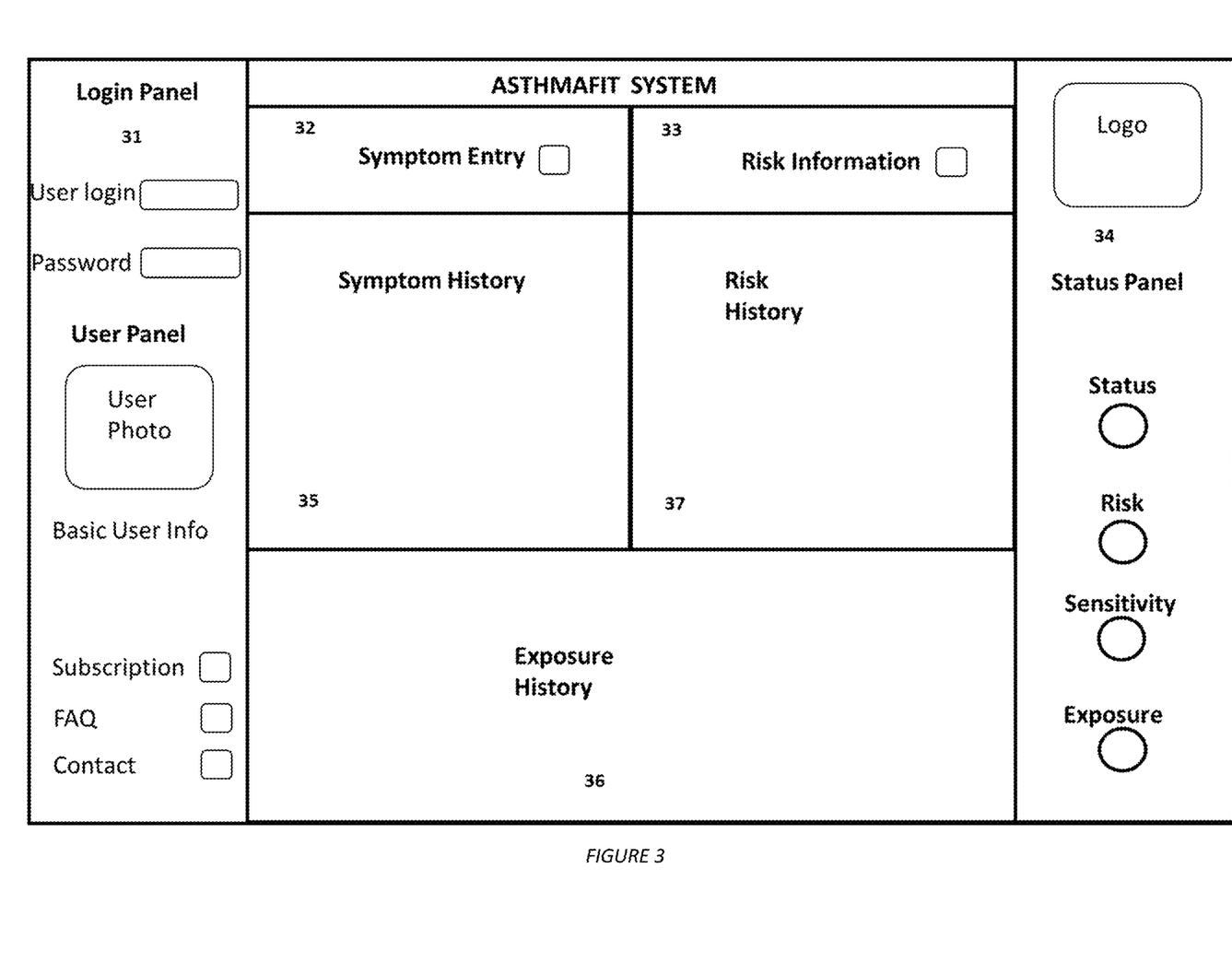
FIG. 3 is a schematic of a user interface of the AMA of a mobile phone device, including a login panel 31, a symptom entry interface 32, a risk information panel 33, a status panel 34, a symptom history panel 35, an exposure history panel 36, and a risk history panel 37.

The wearable air-quality device 11 measures exposure data 12 about the user's exposure in terms of at least one of a pollutant, particulate, and pollen. The exposure data is packaged by the wearable air-quality device 11 and sent to the AMA 15 which is in the mobile device 14 via, a wireless communication such as, for example, Bluetooth communication between the Bluetooth 13 of the wearable air-quality device 11 and a Bluetooth (not shown) of the mobile device 14. The user which suffers from the asthma condition can enter their asthma related symptoms 16 to an asthma symptom interface. The frequency of the entering of the symptoms may differ. For example, the frequency of entering the asthma symptoms 16 may be controlled by the AMA 15 and may be adjusted depending on the severity of the asthma condition of the user. Thus, for users with more severe asthma condition the AMA 15 may prompt the users to enter data more frequently than users with less severe asthma condition. The user may be prompted by the AMA 15 to enter their symptoms by answering a specific questionnaire designed specifically to collect key symptom data for the asthma condition of the user which in combination with the exposure data may then be analyzed in order for the system to provide an asthma risk assessment to the user. Referring to FIG. 3, for example, the ASTHMAFIT system may provide a symptom entry user interface 32 which once touched by the user may open as shown, for example, in FIG. 4 in a new window.

The AMA 15 may be configured to perform some or all of the following: reading and processing exposure data received from the wearable air-quality device, for enabling direct symptom data entry by the user, for sending the exposure and symptom data to a database of the CPP 17 via a communication device of the mobile device, accepting data from a database of the CPP 17, presenting a health status including respiratory health and at least one of dietary instructions, sleep, activity, and stress measures to the user, presenting a health prognosis including some aspect next day warnings, and means for managing user subscription and access to the ASTHMAFIT system including making payments.

According to the illustrated embodiment of FIG. 1, the total collected data (exposure and symptom) for the user are delivered to the CPP 17 consisting of databases and software. The cloud processing platform 17 may receive data from other users 111. The cloud processing platform 17 may receive data from other external sources 18. The data form other external sources 18 may include, for example, data from local meteorological stations, e.g., temperature and humidity, data from local air quality monitoring stations, e.g., gas pollutants and particulates, data from air quality surveys, e.g., from mobile units, pollen data from air trap devices). The cloud database may include databases for storing: user symptom histories, user life-style histories (e.g., dietary, sleep, stress), user sensitivity matrix, and user exposure/symptom correlation data. The databases may further store external broad region data for environmental conditions including temperature and humidity, pollen and particulates from air-quality analysis stations, and even satellite data. These data may be used to complement, enhance, validate, and scale-correct the data obtained from the wearable air-quality device. The databases are configured to also provide and store data to and from the cloud software.

An individualized asthma risk report 19 for the user may be generated from the cloud system and sent to the user providing feedback on their condition and associated risks. The asthma risk report 19 may include, for example, an individualized asthma risk analysis and at least one warning, for example, to avoid a certain high pollen area the next day or at a certain future time within the next few days. An example of the asthma risk report 19 is shown in FIG. 5. The user enters at least one anticipated level of activity in terms of duration and intensity E in the Activity Risk Matrix 51. The color scale of the element of the activity risk matrix corresponding to the user's anticipated activity is associated to a risk indicated in the Risk Scale 52. The user enters at least one of the anticipated locations of their visits, e.g. A, B, C, D in the Location Risk Map 54 which is a map centered around a location selected in the Location Select 53. The Activity and Location risks are then automatically reflected in a Net Next-Day Risk 57 indicator which also follow the Risk Scale 52. Also, depending on the user's recent history of symptoms and other activities, additional warnings may be provided in the Warnings and Recommendations panel 56.

Referring to FIG. 5, the asthma risk report 19 may include an activity risk matrix 51, a risk scale 52, a location risk map 54, warnings and recommendation 56, and a net next day risk 57. The user may also by selecting a more detailed report button 58 access another window with more detailed risk information. (e.g., details related to the user's individual contributions to the Activity and Location risk inputs into the net Next-Day Risk 57, details related to the risk/projected symptom correlations of the cloud software, justifications for the provided messages in the Warnings and Recommendations panel 56)

Referring to FIG. 2A, an example of the wearable air-quality device is provided which may be used with the asthma management system. The wearable air-quality device is in the shape of a wearable watch 20 which can be secured on the wrist of the user via a band 29 for measuring a user's exposure to at least one of an environmental pollutant, particulates, and pollen. The wearable air-quality device 20 as illustrated in FIG. 2A may comprise a first sensor 21. The first sensor may be a sensor for measuring one pollutant (e.g., ozone, $O_3$, nitrous oxides, NOx, Sulphur dioxide $SO_2$, volatile organic compounds, VOCs). An additional sensor 22 for measuring an environmental condition such as temperature, or humidity may also be employed. The wearable air-quality device 20 may also include a sensor 23 for measuring particulates including pollen of different size. The third sensor 23 may include means for sampling the ambient air through an inlet 28 with a controlled flow rate which may consist of a fan 24 internally controlled by the microprocessor 210 to provide a constant flow of ambient air into the measurement area of the sensor for rapid and accurate measurements. The same arrangement for sampling air may be employed with the first and second sensors. Preferably, the air sampling inlet and fan may be shared commonly by the first, second, and third sensors 21, 22, 23 for increasing the compactness of the wearable, air quality device 20. The wearable air-quality device 20 may further include a rechargeable battery 25, an LED indicator light 26, and a communication system 27 such as, for example, bluetooth. However, any compact suitable data transceiver may be used. The rechargeable battery 25 may be of any suitable compact type for providing sufficient power for the operation of the various sensors, the microprocessor, the fan, and the LED indicator light. The second sensor 22 may be a multisensory capable of measuring more than one gas pollutants. Any suitable, commercially available sensors may be used.

FIG. 2B depicts an embodiment where the particulates/pollen sensor 23 is a modified optical module (top and side view). The air inlet to the optical chamber includes a flap F that changes position periodically altering the airflow path and thus its intersection with the laser path-line 30 changes. The laser 210 and sensor 211 locations remain unchanged in the modified optical module. When the flap F is positioned to block the A airflow path then the air flow is directed through the B airflow path corresponding to a conventional (i.e., as employed in commercial optical sensors) configuration. On the other hand, when the flap position blocks the B airflow path then the air flow is directed through the A airflow path. The airflow paths A and B intersect the laser path-line 30 at different positions 212 and 213, leading to different scattering angles, OA and OB, respectively. Therefore, the same sensor 211 element will receive a different signal from different scattering angles and thus particle sizes. With a suitable configuration the detection range of airpath B (e.g., 0.5-10 μm) can be switched to the detection range of airpath A (e.g., 10-100 μm) simply by switching the flap position. Thus, the difference in the sensor element signal can then be corrected by simply adjusting the corresponding particle size by a correction factor (according to established light scattering theory) that depends entirely on particle size and geometry of the configuration.

Referring to FIG. 3, the AMA may include several interfaces including a login panel 31, a symptom entry interface 32 (See FIG. 4), a risk information panel 33 (See FIG. 5), a status panel 34, a Symptom History Graphics 35, an Exposure History Graphics 36, and a Risk Information History Graphics 37. The key features of an example of the main interface of the AMA are shown in FIG. 3. The application may include different user interfaces adapted for different users. For example, a user symptom interface may be different for a child, and for an adult. The AMA may also include an interface for a care-giver (e.g., a parent, or a nurse). The login panel 31 may ask for a user and password id for the user to access the AMA. The AMA may also include a payment or subscription function. The AMA enables user direct symptom data entry via 32 (See FIG. 4). The AMA may send and receive data to the cloud processing platform 17 via a communication network (e.g., internet). In FIG. 5 an example of a location risk map is provided.

The status panel 34 includes a status indicator, risk indicator, a sensitivity indicator and an exposure indicator. The status panel indicators provide indications based on a common color code (i.e., "green" indicating a good condition, "orange" indicating an average condition, "red" indicating a bad condition). The status indicator may reflect the general condition of respiratory health of the user. The risk indicator may present the next-day risk of the user. The sensitivity indicator may provide the status of the user's sensitivity to triggers. The Exposure indicator my provide an indication of the user's current or recent exposure to at least one of the 3Ps. The user panel may also include a display for displaying a photo of the user and may further include a display with the user basic info. A subscription button may be used by the user for accessing their subscription account. An FAQ button may allow the user to find answers to frequently asked questions about the system and, or their data including exposure history data and symptom history data. A contact button allows the user to find contact information about their physician, local emergency clinics and a help-line for asthma patients.

Figure 4:
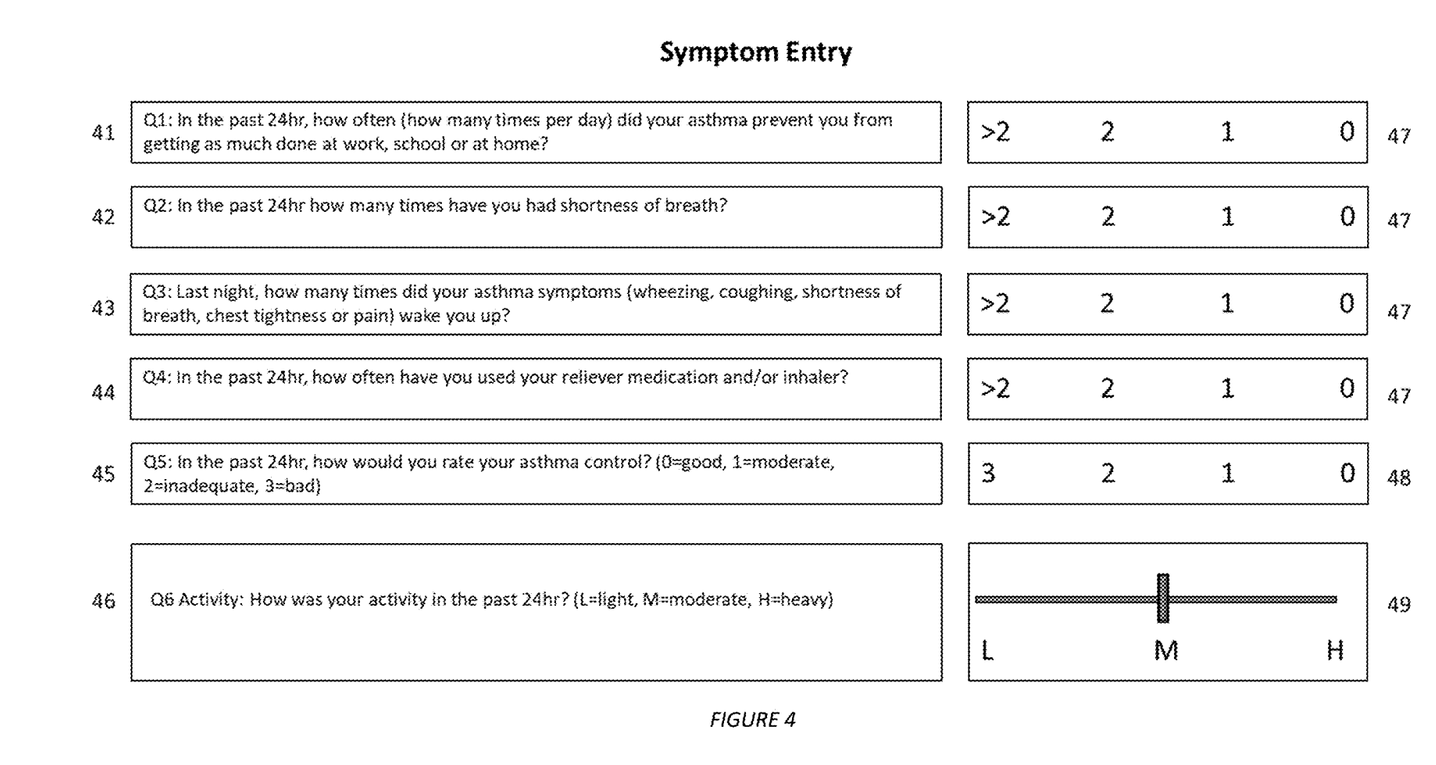
FIG. 4 is a schematic of a symptom entry interface related to user symptom entry.

Referring to FIG. 4, in an embodiment of the invention, symptom information is entered by the user into the AMA on a regular basis. Data may relate to asthma symptoms. However, in other embodiments, symptom data may also include, besides asthma symptom data, other data about the user including sleep and dietary habits, stress levels, and activity such as walking and running. Specifically, the questionnaire seeks to establish the frequency of breathing difficulties during the last 24 hours Q2, the frequency with which asthma symptoms interfered with normal activities Q1, the frequency with which asthma symptoms interrupted sleep the previous night Q3, the number of times medication and/or inhaler was used Q4, the overall rate of asthma control Q5, and a report of physical activity over the last 24 hours Q6. For these questions a user-friendly reporting system is employed in which the user answers in terms of the frequency via zero (0), one (1), two (2), and more than two (>2). For the asthma control question the user ranks the control as (0=good, 1=moderate, 2=inadequate, 3=bad) and for the activity report the user positions a slider between L=low, M=moderate, and H=high. The definitions of low, moderate and high activity may differ depending on the age of the user. The AMA may provide the user a list of activities and a rating of the activity as low, moderate, or high depending on the type of activity and its time duration. For example, the AMA may provide an activity list, with walking listed as an activity and divided into low pace and high pace walking. For low pace walking the AMA activity list may provide that walking at low pace for a time period of from about 10 minutes to about 30 minutes may be rated as low activity, walking at low pace for more than about 30 minutes but less than about 60 minutes may be rated as moderate, and walking at low pace for more than about 60 minutes may be rated as high. Low pace walking may be defined, for example, walking at a pace of 3 miles per hour and high pace walking may be defined as walking at a pace of more than 3 miles per hour. Other activities such as running, commuting by bus, working outdoors and the like may be included in the activity list which the user may consult for determining their level of activity for the day before entering the level of activity as low, medium or high by moving the slider in answering Q6 of the symptom entry interface.

Referring to FIG. 5 in an embodiment of the invention elements of the risk information and warning report generated by the system for an individual user are shown. The activity risk matrix 51 displays the risk in terms of a shaded gray-scale code 52 according to the expected next-day duration and intensity of the user's activity as selected by the user with the white dot E. The risk report also provides a map centered around a selected location 53 indicating the expected localized risk in the area 54. This map provides the risk from the net exposure to the 3Ps, is specific to the user, and varies every day. To compute this risk, maps for each individual pollutant, particulate, pollen are determined which are identical for every user but change every day. This set of maps leads to a risk map due to exposure to the 3Ps which differs for each user due to their different exposure and symptom histories and the user sensitivity. The user selects expected location or locations on the map where they expect to go the next hours or day (indicated A, B, C, and D). The overall net next day risk, based on the user's selections in the activity risk matrix 51 and user's selections in the location risk map 54, is indicated in a shaded risk bar 57 following the risk scale 52. The net next-day risk is determined from these user selections, e.g., multiple daily activities, multiple location sites, by the risk analysis software 72c based on internal algorithm parameters for the user. Additional warnings and recommendations are provided in a box 56 in the form of plain text messages, e.g., W1 and W2 which are generated by the system based on the overall net next day risk. For example, W1 may advise the user to "reduce activity duration" in the next day due to high risk based on the analysis of the user's recent exposure and symptom data. W2 may advise the user to "limit activity duration at locations A and D" because the system has determined a high risk based, for example, on the analysis of the other data 18 which show high pollen, temperature, and pollution in these locations the next day. Additional information may be provided to the user regarding details of the risk analysis by the user clicking on the "more details" arrow 58 which opens a new window with more details. For example, details may be related to the user's individual contributions to the Activity and Location risk inputs into the net Next-Day Risk 57, may be related to the risk/projected symptom correlations of the cloud software, may be justifications for the provided messages in the Warnings and Recommendations panel 56.

Referring to FIG. 6 according to an embodiment of the invention the user may access the AMA on a daily basis to establish their risk and enter symptom information. The user may connect to the AMA installed on a smart phone or tablet typically at the start of the day at 601. The user accesses the risk information panel in the AMA at 602. The user enters their expected activity (i.e., duration and intensity) at 603 on the Activity risk matrix 51. The user also enters their expected next day locations at 604 by indicating locations on the Daily risk map 54. For example, the selection of the locations may be done by simply touching one or more points of the Daily risk map 54. The user is informed by the system about the next day warnings and risk at 605. Once the user becomes aware of the total risk and is informed of the potential warnings at 605 may then modify their actions for the day at 606. The user may then disconnect from the AMA at 607 and wears the device during outdoor activities at 608. At the end of the day, the user connects to the AMA via smart phone/tablet at 609, to enter their symptom information at 610 by answering a questionnaire (see FIG. 4) generated by the AMA. The user may at any time enter the AMA to access historical (e.g., previous 10 days) symptom, exposure, and risk information. The user may then disconnect at 611.

Figure 7:
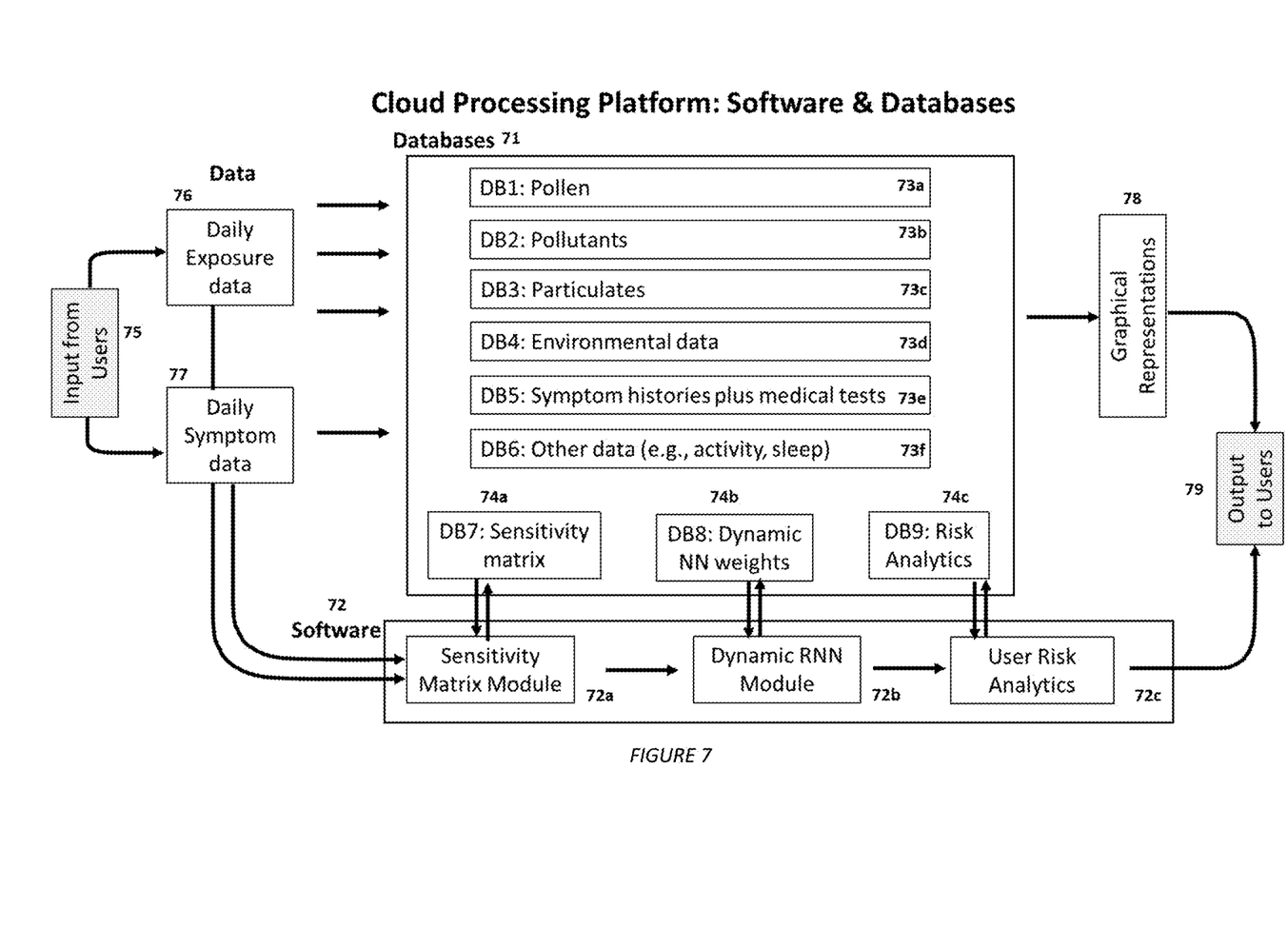
FIG. 7 depicts a diagram of the cloud software and databases, including processing of exposure data 76, processing of symptom data 77, databases 71, software 72, Graphical Representations 78, data input from the AMA 75 and data output to the AMA 79.

Referring to FIG. 7, an example of the cloud processing platform 17 is provided. The platform 17 includes data input and processing from one or more users 75 including daily exposure data 76 and daily symptom data 77. The databases 71 store data as individual databases including: data relative to pollen exposure 73a, data relevant to pollutant exposure 73b, data relevant to particulate exposure 73c, 73b, environmental data (e.g., temperature and humidity) 73d, symptom data (including medical tests) 73e, other data (e.g., activity, sleep) 73f, and databases containing software intermediate data, i.e., sensitivity matrix component values 74a, dynamic neural net weights 74b, and risk analytics 74c. Databases 73a, 73b, 73c, 73d may include data from external air quality stations. The cloud-software 72 may comprise three key modules, i.e., a sensitivity matrix module 72a, a dynamic neural network module 72b (e.g., recurring neural net), and the user risk analytics module 72c. Graphical representations, e.g., line-plots, of data (e.g., for pollen, pollutants, particulates, environmental data, symptoms), are generated on a moving time range (i.e., from 10 days to 1 year) and consist of daily values, 5 day smoothed values, cumulative values 78. The output from the software 72 together with graphical representations 78 of the current status and historical exposure and symptom histories of the user are output to the user 79 via the AMA in the user smart phone or tablet.

Although the present invention has been described with specific embodiments, these embodiments are provided for explanation of the invention to the skilled person and are not intended to limit the scope of the invention which is defined in the accompanied claims.

For example, although the system has been described with specific embodiments relating to an asthma condition, it should be understood that the system may also be employed for other respiratory diseases including allergic rhinitis, Chronic Obstructive Pulmonary Disease, or COPD.

The system may be used for any respiratory disease exhibiting an exacerbation due to environmental exposure, e.g., pulmonary fibrosis, cancer post treatment, cystic fibrosis etc.

What is claimed is:

1. A system for intelligent monitoring and management of asthma of a user of the system, the system comprising:

a wearable air quality device in the form of a hand-watch and includes a band for securing the wearable air-quality device to a hand of the user, comprising a first sensor that measures a concentration of at least one gas pollutant in ambient air, a second sensor that measures environmental data including temperature and humidity of the ambient air, and a third optical sensor that measures particulates including pollen in the ambient air, a battery that powers the wearable air-quality device, a communication device that communicates the collected exposure data to an asthma management application, a microprocessor that controls the operations of the wearable air-quality device, an inlet for sampling the ambient air, a fan that provides a controlled flow rate of ambient air from the inlet of the third optical sensor to a sensing area of the third optical sensor, and an energy management system that intermittently controls the fan to minimize energy consumption of the battery;

a mobile device of the user on which is installed the asthma management application; and a cloud processing platform, wherein the wearable air quality device collects user exposure data comprising the concentration of the at least one gas pollutant, the temperature and humidity, and the concentration of the particulates and pollen in the ambient air, and transmits the collected user exposure data to the asthma management application via the communication device, wherein the asthma management application includes a user symptom interface that receives asthma symptom data from the user, including a frequency of breathing difficulties the user experienced during the last 24 hours, wherein the asthma management application receives the user exposure data from the wearable air-quality device, and transmits the user exposure data and the asthma symptom data to the cloud-based processing platform, wherein the cloud processing platform includes at least one cloud database and at least one cloud software that stores and processes the user exposure and the asthma symptom data, analyzes the user exposure data, the asthma symptom data, and the data in the at least one database, and provides a risk analysis report to the user via the asthma management application, the risk analysis report including a visual display in a screen of the asthma management application of a next-day risk based on a location the user selects to visit the next day and a level of activity planned by the user in the selected location, wherein the at least one gas pollutant is one of ozone $O_3$, sulfur dioxide $SO_2$, nitrogen oxides $NO_x$, volatile organic compounds VOCs, ammonia $NH_4$, carbon dioxide $CO_2$, and carbon monoxide CO, wherein the risk analysis report further includes recommendation on whether the user should reduce a duration of a planned next-day activity, or limit duration of exposure at the selected location, and wherein the user mobile device is a smart phone, wherein the at least one cloud database stores:
  a pollen database storing the user pollen concentration data,
  a gas pollutant database storing the user gas pollutant concentration data,
  a particulates database storing the user particulates concentration data, and
  an environmental data database storing the user temperature and humidity data,
  an asthma symptom database storing the user asthma data, wherein the at least one cloud database provides and stores data to and from the cloud software, and wherein the cloud software comprises:
  a sensitivity matrix module that calculates a sensitivity of the user to various asthma symptom triggers based on the recent cumulative user exposure data and the user symptom data;
  symptom/exposure correlation software that correlates exposure to symptom histories, and predicts next day conditions of the user based on their current sensitivity matrix and next day weather predictions;
  a risk analysis module employing a risk matrix that correlates user asthma symptoms with user activity including intensity and duration of the user activity, and generates a location-based estimate of asthma risk, by taking into account the user exposure data and the user exposure symptom data and the calculated user sensitivity to the various asthma symptom triggers,
  wherein the cloud software further determines pollen type and concentration levels based on historical pollen data including monthly averaged pollen type and concentration, and historical environmental data including temperature and humidity, by employing Machine Learning regression approaches for the current month and environmental data.

2. The system of claim 1, wherein the optical sensor includes:
an optical chamber;
a laser;
a sensor, and
an air inlet leading to the optical chamber, wherein the air inlet includes a flap that changes position periodically altering the airflow path between a first and a second air flow paths so that an intersection of any particulates in the air flow with the laser path-line changes leading to different scattering angles thus allowing detecting and measuring particulates of sizes in the first air path of 10 to 100 µm, and in the second air path of 0.5 to 10 µm.

3. The system of claim 2, wherein the third sensor of the wearable air-quality device includes an energy management system for intermittent operation of the airflow fan to minimize energy consumption.

4. The system of claim 1, wherein the asthma management system further provides to the user next-day warning with additional risk analysis metrics based on outdoor planned activity at a specific location and a duration and intensity of the planned physical activity of the user at the specific location.

5. The system of claim 1, wherein the asthma management application prompts the user to enter asthma symptom information by answering an asthma specific questionnaire.

6. The system of claim 1, wherein the asthma management application includes different asthma symptom user interfaces for at least two of the following groups of people, minors, adults, elderly, and for care-givers including for parents and nurses.

7. The system of claim 1, wherein the sensitivity matrix module further uses dietary, sleep, and stress information of the user, and spirometry test data including FEV1 and allergy scans for estimating an initial sensitivity profile of the user, and uses the initial sensitivity profile of the user in the calculating of the sensitivity of the user to the various asthma symptom triggers.

8. The system of claim 1, wherein the system monitors and manages asthma of a plurality of users, the system further comprising the following software:
  software creating environmental exposure maps based on user exposure data from multiple users;
  projection software generating next day environmental exposure maps based on the extrapolation of historical exposure maps from previous 3 days or more; and
  initialization software that employs multi-user data from other similar regions to determine initial values of the sensitivity matrix and/or the correlation parameter values for a new location.

9. The system of claim 8, wherein a user's risk is dynamically updated during the day by including the user's real-time exposure data and providing real-time warnings.

10. The system of claim 8, wherein a user's risk is dynamically updated by updating real-time the multi-user generated environmental exposure maps providing improved accuracy estimates of asthma risk in real-time.

11. The system of claim 8, where data from a grid of stationary air-quality sensors are integrated into the system in order to validate and improve the system's environmental exposure maps and also for enabling the development of coarse-scaled environmental exposure maps when users are insufficient in number.

12. A method for management, prediction, and warning of an asthma condition of an asthma patient user, the method comprising:
  collecting user exposure data including a concentration of at least one gas pollutant in ambient air via a first sensor, environmental data including temperature and humidity of the ambient air via a second sensor, and a concentration of particulates and pollen in the ambient air via a third optical sensor, wherein the sensors are installed in a wearable air-quality device having a form of a hand-watch secured to the hand of the asthma patient user via a band;

transmitting the collected user exposure data to an asthma management application loaded on a mobile device of the asthma patient user, or of a care provider of the asthma patient user, via a communication device including a data transceiver installed on the wearable air-quality device;

collecting daily asthma symptom data of the asthma patient user including a frequency of breathing difficulties the user experienced during the last 24 hours by using a user symptom interface of the asthma management system including an asthma questionnaire which is filled by the asthma patient or the care provider of the asthma patient;

processing the exposure data and the symptom data by the asthma management application including compressing the environmental and the symptom data;

transmitting the processed exposure data and the user asthma symptom data to a cloud processing platform for storing and analysis; and generating a risk analysis report for the asthma patient user;

transmitting the risk analysis report to the asthma management application of the asthma patient user where it can be accessed by the asthma patient, wherein the risk analysis report includes a visual display in a screen of the asthma management system of a next-day risk based on a location the user selects to visit the next day and a level of activity planned by the user in the selected location, wherein the cloud processing platform includes at least one cloud database and at least one cloud software that stores and processes the user exposure and the asthma symptom data, analyzes the user exposure data, the asthma symptom data, and the data in the at least one database, to provide the risk analysis report to the user via the asthma management application, wherein the at least one gas pollutant is one of ozone $O_3$, sulfur dioxide $SO_2$, nitrogen oxides $NO_x$, volatile organic compounds VOCs, ammonia $NH_4$, carbon dioxide $CO_2$, and carbon monoxide CO, wherein the risk analysis report further includes recommendation on whether the user should reduce a duration of a planned next-day activity, or limit duration of exposure at the selected location, and wherein the user mobile device is a smart phone, wherein the at least one cloud database stores:
  a pollen database storing the user pollen concentration data,
  a gas pollutant database storing the user gas pollutant concentration data,
  a particulates database storing the user particulates concentration data, and
  an environmental data database storing the user temperature and humidity data,
  an asthma symptom database storing the user asthma data, wherein the at least one cloud database provides and stores data to and from the cloud software, and wherein the cloud software comprises:
  a sensitivity matrix module that calculates a sensitivity of the user to various asthma symptom triggers based on the recent cumulative user exposure data and the user symptom data;
  symptom/exposure correlation software that correlates exposure to symptom histories, and predicts next day conditions of the user based on their current sensitivity matrix and next day weather predictions;
  a risk analysis module employing a risk matrix that correlates user asthma symptoms with user activity including intensity and duration of the user activity, and generates a location-based estimate of asthma risk, by taking into account the user exposure data and the user exposure symptom data and the calculated user sensitivity to the various asthma symptom triggers, and wherein the cloud software further determines pollen type and concentration levels based on historical pollen data including monthly averaged pollen type and concentration, and historical environmental data including temperature and humidity, by employing Machine Learning regression approaches for the current month and environmental data.

* * * * *